US011693489B2

(12) United States Patent
Hitzelberger et al.

(10) Patent No.: US 11,693,489 B2
(45) Date of Patent: Jul. 4, 2023

(54) CONTACTLESS OPERATION OF MEDICAL DEVICES USING A POINTING APPARATUS

(71) Applicants: Fresenius Medical Care Deutschland GmbH, Bad Homburg (DE); Fresenius Medical Care AG & Co KGaA, Bad Homburg (DE)

(72) Inventors: Christoph Hitzelberger, Saarlouis (DE); Waldemar Witt, Darmstadt (DE); Martin Pospiech, Darmstadt (DE)

(73) Assignees: Fresenius Medical Care Deutschland GmbH, Bad Homburg (DE); Fresenius Medical Care AG & Co KGaA, Bad Homburg (DE)

(*) Notice: Subject to any disclaimer, the term of this patent is extended or adjusted under 35 U.S.C. 154(b) by 0 days.

(21) Appl. No.: 17/677,069

(22) Filed: Feb. 22, 2022

(65) Prior Publication Data
US 2022/0326786 A1    Oct. 13, 2022

(30) Foreign Application Priority Data
Apr. 9, 2021  (EP) .................................... 21167557

(51) Int. Cl.
*G06F 3/0346*    (2013.01)
*G16H 40/63*     (2018.01)
(Continued)

(52) U.S. Cl.
CPC .......... *G06F 3/0346* (2013.01); *G06F 3/0304* (2013.01); *G06F 3/0383* (2013.01);
(Continued)

(58) Field of Classification Search
CPC ..... A61B 5/0507; A61B 5/1172; A61B 5/318; A61B 5/7475; A61M 2205/3306;
(Continued)

(56) References Cited

U.S. PATENT DOCUMENTS 8,570,274 B1 * 10/2013 McIntosh .............. G06F 1/1698
345/173
2010/0253625 A1  10/2010 Lazarev et al.
(Continued)

FOREIGN PATENT DOCUMENTS

DE    102019002278 A1    10/2020
WO    WO 99/008128 A1    2/1999
(Continued)

OTHER PUBLICATIONS

"Frequency-Modulated Continuous-Wave Radar (FM-CW Radar)" https://web.archive.org/web/20140412103831/http://www.radartutorial.eu/02.basics/Frequency%20Modulated%20Continuous%20Wave%20Radar.en.html (Apr. 8, 2014).
(Continued)

*Primary Examiner* — Chun-Nan Lin
(74) *Attorney, Agent, or Firm* — Leydig, Voit & Mayer, Ltd.

(57) ABSTRACT

Contactless operation of a medical device, such as a hemodialysis (HD) or peritoneal dialysis (PD) device, is provided via a mobile pointing apparatus and a receiving arrangement associated with the medical device. The mobile pointing apparatus includes a signal emitter for emitting an optical or electromagnetic signal, and the receiving arrangement associated with the medical device determines a pointing target of the mobile pointing apparatus relative to the medical device based on the signal emitted by the mobile pointing apparatus and triggers a function of the device based on the pointing target of the mobile pointing apparatus.

8 Claims, 3 Drawing Sheets

(51) Int. Cl.
  *G06F 3/03* (2006.01)
  *G06F 3/0354* (2013.01)
  *G06F 3/038* (2013.01)
  *G06V 40/13* (2022.01)
  *A61B 5/00* (2006.01)
  *A61M 5/172* (2006.01)

(52) U.S. Cl.
  CPC ...... *G06F 3/03542* (2013.01); *G06F 3/03545* (2013.01); *G16H 40/63* (2018.01); *A61B 5/7475* (2013.01); *A61M 5/172* (2013.01); *A61M 2205/3306* (2013.01); *A61M 2205/502* (2013.01); *G06V 40/13* (2022.01)

(58) Field of Classification Search
  CPC . A61M 2205/502; A61M 5/172; G01S 13/82; G01S 13/878; G06F 3/0304; G06F 3/0346; G06F 3/03542; G06F 3/03545; G06F 3/0383; G06V 40/13; G16H 40/63
  See application file for complete search history.

(56) References Cited

U.S. PATENT DOCUMENTS

| | | | |
|---|---|---|---|
| 2012/0326979 | A1 | 12/2012 | Geisert et al. |
| 2017/0097413 | A1* | 4/2017 | Gillian .................. G01S 7/4004 |
| 2020/0027275 | A1 | 1/2020 | Wan |
| 2020/0371606 | A1 | 11/2020 | Shim et al. |
| 2021/0369928 | A1* | 12/2021 | Wiktor .................. G16H 40/63 |
| 2022/0096007 | A1* | 3/2022 | Robinson ............. A61B 5/7285 |

FOREIGN PATENT DOCUMENTS

| | | |
|---|---|---|
| WO | WO 2007/009833 A1 | 1/2007 |
| WO | WO 2008/042220 A2 | 4/2008 |
| WO | WO 2016/204641 A1 | 12/2016 |
| WO | WO 2018/167777 A1 | 9/2018 |
| WO | WO 2020/127177 A1 | 6/2020 |

OTHER PUBLICATIONS

Pasquariello et al., "Remote-Touch: A Laser Input User-Display Interaction Technology," *J. Display Technology*, 4(1), 39-46 (Mar. 2008).

Wolff, Christian "Frequency Modulated Continuous Wave Radar (FMCW Radar)," www.radartutorial.eu (2018).

European Patent Application No. 21 16 7557, Search Report (dated Sep. 29, 2021).

International Patent Application No. PCT/EP2022/059474, Search Report (dated Oct. 27, 2022).

* cited by examiner

CONTACTLESS OPERATION OF MEDICAL DEVICES USING A POINTING APPARATUS

CROSS-REFERENCE TO RELATED APPLICATIONS

Priority is claimed to European Patent Application No. EP 21167557.4, filed on Apr. 9, 2021, the entire disclosure of which is hereby incorporated by reference herein.

TECHNICAL FIELD

Exemplary embodiments of the present invention relate to apparatuses and methods for the contactless operation of medical devices.

BACKGROUND

Special hygiene standards apply to medical devices in order not to endanger the patients treated with these devices by transmitting pathogens. In everyday clinical practice, such devices are operated by different medical staff. The same staff is also involved in actions on different patients. There is a risk here that pathogens such as viruses and bacteria, irrespective of their source (patient, staff, visitors, etc.), are transmitted to patients and/or medical staff via the operating surfaces of the medical devices to which they have been applied by touch, thus endangering the health of persons, especially of patients who are already impaired.

To prevent (cross-) contamination via such devices, extensive hygiene measures are usually taken. These consist in particular in the wearing of disposable gloves by medical staff, which are discarded after an action on the patient and/or a medical device interacting with this patient and replaced by new sterile gloves. This constant changing of gloves is expensive and time-consuming, especially in clinics, intensive care units or dialysis centers. Furthermore, there is a need for a high hand disinfection rate among medical staff. This measure is also expensive and time-consuming due to the necessary use of disinfectants and is potentially harmful to the skin of the staff. In addition, there is also a need to disinfect medical devices frequently. Touchscreens in particular need to be disinfected very frequently. In addition to the disadvantages mentioned above, this causes damage to the touchscreen over time due to the disinfectants used and the mechanical wear caused by the actual disinfection activity due to, for example, the wiping motion with cloths during disinfection.

There is therefore a desire to avoid touching medical devices as much as possible. In the state of the art, voice control and gesture control methods are known for this purpose. However, both methods are not very user-friendly and intuitive in everyday clinical use. Voice control is problematic in busy environments with background noise and is also disadvantageous with regard to the private patient-related character of the information entered. Gesture control requires extensive staff training and is often cumbersome and ill-suited to the dynamic daily routine within medical facilities.

From U.S. Pat. No. 8,570,274 B1 it is known to use a pointing stick apparatus for contactless control of a user interface in a personal computer. In the embodiment described in detail, the pointing stick apparatus communicates with receivers installed on the laptop via ultrasound. However, this device is of only very limited use for the requirements characteristic of medical technology mentioned at the outset.

SUMMARY

In an exemplary embodiment, the present invention provides a system for contactless operation of a medical device. The system includes: an optical pointing apparatus, comprising an optical signal emitter configured to emit a directional light signal; one or more optical sensors configured to determine a pointing target of the optical pointing apparatus relative to the medical device based on the directional light signal emitted by the optical pointing apparatus; and a processor configured to trigger a function of the medical device based on the determined pointing target of the optical pointing apparatus.

In a further exemplary embodiment, the medical device comprises a hemodialysis device, a peritoneal dialysis device, an infusion pump, a medical monitoring apparatus, an electrocardiogram (ECG) device, a medical ultrasound device, a cell separation apparatus, or a heart/lung machine.

In a further exemplary embodiment, the directional light signal is a laser signal.

In a further exemplary embodiment, the one or more optical sensors comprises one or more phototransistors and/or one or more photodiodes.

In a further exemplary embodiment, at least a part of the medical device comprises a coating for redirecting the directional light signal emitted by the optical pointing apparatus to the one or more optical sensors.

In a further exemplary embodiment, the medical device comprises operating components and a transparent cover for the operating components, wherein the coating is at least partially disposed on the cover.

In a further exemplary embodiment, the optical signal emitter is configured to emit light in the non-visible spectrum, and the optical pointing apparatus further comprises a second optical signal emitter configured to emit light in the visible spectrum.

In a further exemplary embodiment, the optical pointing apparatus further comprises: at least one push-button; and a modulator configured to modulate information on the directional light signal emitted by the optical signal emitter in response to actuation of the at least one push-button.

In a further exemplary embodiment, the optical pointing apparatus further comprises a fingerprint scanner and/or a communication device configured to communicate with a fingerprint sensor wearable under a glove of an operator.

In a further exemplary embodiment, the one or more optical sensors are arranged at the medical device or arranged remotely relative to the medical device with a defined spatial relationship thereto.

In another exemplary embodiment, the present invention provides a system for contactless operation of a medical device. The system includes: an electromagnetic pointing apparatus, comprising at least one electromagnetic signal emitter configured to emit a radar signal; at least three receivers configured to receive the radar signal emitted by the at least one electromagnetic signal emitter; and a processor configured to: determine a pointing target of the electromagnetic pointing apparatus relative to the medical device based on the received radar signal; and trigger a function of the medical device based on the determined pointing target of the optical pointing apparatus.

In a further exemplary embodiment, the processor is further configured to compare the radar signal with a reference signal.

In a further exemplary embodiment, the system further includes: an electromagnetic signal emitter associated with the medical device configured to emit a trigger signal to cause the electromagnetic pointing apparatus to emit the radar signal from the at least one electromagnetic signal emitter.

In a further exemplary embodiment, the processor is configured to perform a frequency modulated continuous wave (FMCW) method for determining a distance between the at least one electromagnetic signal emitter of the electromagnetic pointing apparatus and the at least three receivers.

In a further exemplary embodiment, the electromagnetic pointing apparatus further comprises at least a second signal emitter configured to emit a second radar signal and/or a sensor for determining an inclination of the electromagnetic pointing apparatus, and the electromagnetic pointing apparatus is further configured to determine a pointing axis of the electromagnetic pointing apparatus.

In a further exemplary embodiment, the electromagnetic pointing apparatus further comprises: at least one push-button; and a modulator configured to modulate information on the radar signal emitted by the at least one electromagnetic signal emitter in response to actuation of the at least one push-button.

In a further exemplary embodiment, the electromagnetic pointing apparatus further comprises a fingerprint scanner and/or a communication device configured to communicate with a fingerprint sensor wearable under a glove of an operator.

In a further exemplary embodiment, the at least three receivers are arranged at the medical device or arranged remotely relative to the medical device with a defined spatial relationship thereto.

In yet another exemplary embodiment, the present invention provides a method for contactless operation of a medical device. The method includes: emitting, by an optical signal emitter of an optical pointing apparatus or at least one electromagnetic signal emitter of an electromagnetic pointing apparatus, a directional light signal or a radar signal; determining, using one or more optical sensors or at least three receivers, a pointing target of the optical pointing apparatus or the electromagnetic pointing apparatus relative to the medical device based on the directional light signal or the radar signal; and triggering, by a processor, a function of the medical device in response to the determined pointing target.

BRIEF DESCRIPTION OF THE DRAWINGS

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Exemplary embodiments of the present invention provide apparatuses and methods that allow improved contactless operation of medical devices.

Exemplary embodiments of the invention relate to a system for contactless operation of a device. The system comprises a mobile pointing apparatus, in particular in the form of a pen, and a receiving arrangement (e.g., a receiving system) associated with the device.

The device may in particular be a medical device, i.e. any type of device used in medical technology, for example a hemodialysis device, a peritoneal dialysis device, an infusion pump, a medical monitoring apparatus (such as, for example, an electrocardiogram (ECG) device), a medical ultrasound device, a cell separation apparatus, a heart/lung machine, or any other medical device which utilizes regular operator input during operation.

The mobile pointing apparatus may comprise a signal emitter for emitting a signal. The receiving arrangement associated with the device may comprise means (e.g., a signal receiver) for determining a pointing target of the mobile pointing apparatus relative to the medical device based on the signal emitted by the mobile pointing apparatus, and means (e.g., a processor) for triggering a function of the device in accordance with the pointing target of the mobile pointing apparatus.

Thus, the operation of the (medical) device can be completely contactless. For example, an operator can point the mobile pointing apparatus at certain parts of the (medical device) (e.g. an on/off button) and thereby trigger a corresponding function on the device (e.g. switching on or off). Further exemplary functions include, for example, requesting operating parameters of components of the (medical) device, such as the delivery speed of a pump for a medical fluid or the volume of a fluid container, adjusting a component of the (medical) device, such as the delivery speed of a pump for a medical fluid, interacting with a graphical user interface (GUI) of the (medical) device, and so on. Furthermore, a much more complex functional operation may be achieved, which will be further explained below.

In one possible embodiment, the signal emitter may comprise an optical signal emitter for emitting a directional light signal, in particular a laser signal. The means for determining the pointing target of the mobile pointing apparatus may comprise one or more optical sensors, in particular phototransistors and/or photodiodes. Such an embodiment may be based on a laser pen.

Part of the device may have a coating, in particular a PMMA (polymethylmetacrylate) coating, for redirecting the light signal emitted by the mobile pointing apparatus to the one or more optical sensors. This increases flexibility with regard to the placement of the sensors.

The device can have operating components and a transparent cover for the operating components, whereby the coating is at least partially arranged on the cover. Thus, devices located in housings or behind covers can also be operated, which has hygienic as well as optical reasons.

In another aspect of the invention, the optical signal emitter may be configured to emit light in the non-visible spectrum. The mobile pointing apparatus may further comprise a second optical signal emitter for emitting light in the visible spectrum. This makes the operation particularly robust versus ambient light, while still being able to provide optical feedback.

As an alternative to the laser embodiment explained above, the signal emitter may also comprise a signal emitter for emitting an electromagnetic signal, in particular a radar signal. The means for determining the pointing target of the mobile pointing apparatus may then comprise at least three receivers for receiving the electromagnetic signal emitted by the signal emitter and means (e.g., a processor) for comparing the electromagnetic signal with a reference signal, preferably stored in the device. In this embodiment, the signal communication is very robust, which leads to a particularly reliable operability.

The receiving arrangement associated with the device may comprise an electromagnetic signal emitter for emitting a trigger signal suitable for causing the mobile pointing apparatus to emit the electromagnetic signal from the signal emitter. Thus, for the determination of the position of the mobile pointing apparatus, reflected radar signals are not evaluated, as is conventionally the case, but signals emitted directly by the pointing pen. This allows a particularly stable detection of the signals emitted by the pointing pen. In this case, the means for determining the pointing target of the mobile pointing apparatus are preferably configured to perform a FMCW (frequency modulated continuous wave) radar method for determining a distance between the mobile pointing apparatus and the receiving arrangement associated with the device.

Also, the mobile pointing apparatus may further comprise means (e.g., a pointing axis detection system) for determining a pointing axis of the mobile pointing apparatus. This may be a second signal emitter for emitting an electromagnetic signal, in particular a radar signal, and/or a sensor for determining an inclination of the mobile pointing apparatus, in particular an angle sensor and/or an inclination sensor.

Regardless of the selected type of signal transmission (e.g. laser or radar), the mobile pointing apparatus may further comprise at least one control element, in particular at least one push-button, as well as means (e.g., a modulator) for modulating information on the optical or electromagnetic signal emitted by the signal emitter in response to an actuation of the at least one control element. Thus, in principle, any information can be transmitted to the device, e.g. control commands.

The mobile pointing apparatus may further comprise means (e.g., an identification system) for identifying an operator. These means may comprise a fingerprint scanner or means (e.g., a communication device) for communicating with a fingerprint sensor wearable under a glove of the operator. This ensures secure identification of the operator prior to operation, which counteracts misuse.

The means for determining the pointing target of the mobile pointing apparatus may be connected to the device, in particular arranged on the device. Alternatively, the means for determining the pointing target of the mobile pointing apparatus may be arranged remotely from the device with a defined spatial reference to it, for example at predefined positions in a room. This makes it possible, among other things, to make several devices operable at the same time.

Furthermore, exemplary embodiments of the invention also relate to the individual components explained above in their own right, namely a mobile pointing apparatus, a (medical) device, and/or a receiving arrangement associated with the (medical) device for use in a system as described above. Thereby, these apparatuses have the features of the respective apparatus as described above.

Also provided is a method for contactless operation of a device, comprising emitting a signal by a signal emitter of a mobile pointing apparatus, in particular in the form of a pen, determining a pointing target of the mobile pointing apparatus relative to the device based on the signal emitted by the mobile pointing apparatus by a receiving arrangement associated with the device, and triggering a function of the device in dependence with the pointing target of the mobile pointing apparatus by the receiving arrangement associated with the device. In the method, the mobile pointing apparatus, the device and/or the receiving arrangement associated with the device may be any of the apparatuses described above.

Finally, the invention provides a computer program with instructions that cause the mobile pointing apparatus, the (medical) device and/or the receiving arrangement associated with the medical device to perform the respective method steps explained herein.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device, a medical system, or other devices as discussed herein may be carried out according to instructions stored on and/or applications installed on one or more respective computing devices.

In the following, exemplary embodiments of a system according to the invention for the contactless operation of a medical device, as well as its individual components and corresponding methods, are explained in more detail.

Exemplary embodiments of the present invention provide intuitive control of devices by evaluating a pointing or gesturing movement towards the component of a medical device to be operated and/or towards a surface of a graphical user interface (GUI) thereof.

According to the invention, a mobile or portable pointing apparatus, in particular a pointing pen (PEN), can be used for this purpose. In the following, the principles of the present invention are explained with reference to a pen for the sake of simplicity; however, it is understood that these principles are equally implementable with other form factors. The position of the preferred longitudinal axis of the pen in space is determined. By computational (e.g. vector analysis, geometric calculations) extension of this axis to the surface of the device to be operated, the point of impact of the extension of the determined pen axis on the device surface can be determined. An appropriately configured control device links the point of impact with predefined actions, in particular with the triggering of a function of the medical device. If, for example, it is determined that the point of impact is within the area of a mounted blood pump, e.g. of a dialysis machine, it can be provided that a setting menu for this pump (e.g. for pump rate, start, stop, etc.) is displayed on the GUI. In this way, an operator can select components for operation only by pointing to a device with an appropriately configured pen. This also includes selecting areas on a screen. In this way, touchscreens can be avoided, for example.

To determine the pen axis, the pen is equipped with at least one signal emitter according to exemplary embodiments of the invention.

Embodiment with Laser Emitter

In this embodiment, the mobile pointing apparatus has one, preferably only one, signal emitter in the form of a directed light source, for example in the form of a laser. Analogous to a laser pen, an operator can thus point visibly to components of a device to be operated in order to select them. For this purpose, the device which is to be operated preferably has optical sensors (e.g. phototransistors and/or photodiodes) at corresponding points which can be targeted by an operator.

The sensors can be identified optically (e.g. by outlines or coloring).

In this embodiment with an optical emitter, it is not necessary to determine the position of the preferred longitudinal axis of the pen in space, since the point of impact on the surface of the device to be operated is determined by corresponding optical sensors on the device itself, independently of the position of the pen in space.

In an exemplary embodiment, the pen may be equipped with two light sources that radiate light in (narrow) parallel axes, one of which radiates light in the non-visible spectrum to which the optical sensors of the device are sensitive (e.g. UV laser and visible red). In this way, the operation can be made robust versus ambient light and still provide optical feedback (aiming aid).

A coating can also be applied that redirects optical radiation to distributed optical sensors, for example as explained in: Donato Pasquariello, M. C. J. M. Vissenberg, and Galileo June Destura, "Remote-Touch: A Laser Input User-Display Interaction Technology" J. Display Technol. 4, 39-46 (2008). Such a coating may include a transparent microstructured light-guiding substrate made of polymethyl methacrylate (PMMA). The substrate is structured with a microstructure of pyramid-shaped depressions. When the laser light hits the substrate, it is collected by the microstructure in the PMMA substrate and part of the laser light is reflected to the side parallel to the surface and thus redirected to optical sensors located there, which can thus determine the position of the laser spot. Such an apparatus comprising a transparent PMMA coating present on the surface of a screen can provide the functionality of a touchscreen without the need for touching the screen. In addition, inexpensive and scalable screens can thus be implemented, since, especially for large surfaces, the number of sensors utilized can be significantly reduced.

The same principle of optical redirection can be applied to the entire body of the device. Thus, it is possible to equip an optically transparent cover in front of operating components of a device with the above-mentioned PMMA coating, which intercepts occurring laser radiation and redirects it to optical sensors. In this way, the operator can target components located behind the cover for selection. An example of a medical device having an optically transparent cover is Fresenius Medical Care's 5008 hemodialysis machine. This is equipped with two transparent hinged doors which cover the extracorporeal blood circuit behind them during operation. This is not only for optical reasons but also for reasons of hygiene.

In addition to the selection of components, input of information for the operation of a medical device is also provided. Conventionally, this is realized, for example, via input elements such as switches or buttons on a touchscreen display. In embodiments of the invention, this is achieved with the pointing pen in a contactless manner by the pointing pen having at least one input option, for example a push-button, which can be activated by the operator. The activation has the effect that the emitted light signal is modulated with information. In one example, pulse code modulation may be used, whereby a pulse code switches the signal on and off in an analog manner so as to create a characteristic digital sequence which encodes the information to be transmitted Amplitude modulation may also be used.

The receivers on the medical device (these do not necessarily have to be arranged directly on the device but can also be assigned to it at a distance; see below) are set up to demodulate the light signal. The medical device carries out steps according to the received information.

For example, the transmitted information can be characteristic for the pointing pen. Accordingly, the medical device can allow, deny and/or restrict operability. Accordingly, the user can also identify himself/herself on the pointing pen. Here, for example, the pointing pen may be provided with a fingerprint scanner for authentication, and an identification signal linked to a stored fingerprint may be modulated onto the light signal.

Identification features can, but do not have to be, sent only after activation of the push-button. They can also be sent permanently (i.e. periodically without an activation signal).

The authentication of a user at the pointing pen can be carried out in various ways, for example via a PIN code entry. Alternatively or additionally, in the context of multi-factor authentication, the authentication of the user can be performed via additional peripheral devices. The peripheral device may be carried by the user, may be part of the pointing apparatus or medical device, or may be in data exchange with the pointing apparatus or medical device. For example, it is a wristband, a smartwatch, a smartcard, or a sensor for capturing biometric characteristics of the user.

In another embodiment, a fingerprint sensor (such as marketed as a Micro RF Tag by SK-Electronics Co Ltd) may be used that can be worn under the glove and transmits authentication data via wireless connection (e.g. NFC) to the pointing pen as soon as the hand of the operator comes close to the pointing pen. This ensures, among other things, that a stolen pointing pen is unusable.

The fingerprint sensor preferably contains a two-dimensional arrangement of the above-mentioned passive RFID tags in the dimensions of a fingerprint or a unique fingerprint portion. The fine segmentation by the small tags enables the detection of the fingerprint-defining lines (papillary strips). For this purpose, the sensor is applied to the underside of the fingertip (pressing on by glove and/or self-adhesive). The emission behavior of the individual tags is determined by the respective substrate and its electrical conductivity. The contact or non-contact with the papillary strips creates a characteristic conductivity distribution that leads to the corresponding emission behavior of the individual tags. To control the conductivity, a paste with high wettability between the sensor and the finger can be advantageous; this paste can also contribute adhesively to the attachment of the sensor. If this paste is heat-dependent, especially if it has phase transitions around skin surface temperatures, it can be ensured that the scanned finger is warm, usually that of a real (warm) person, to make misuse more difficult. A gallium-based paste is advantageous in terms of the achievable melting point, electrical conductivity and high wettability, which lead to accurate imaging of the fingerprint. In this embodiment, the pointing pen comprises means (e.g., a communication device, such as an RFID reader) for communication with the sensor. In this way, the pointing pen can read the signals from the emitting tags of the sensor through the glove worn by an operator. From this, the fingerprint can be reconstructed and subsequently used for authentication.

The actuation of the push-button as an input means can transmit a code that can be interpreted as the actuation of a selection means. For example, if the blood pump of a hemodialysis device is selected with the pointing pen, a selection menu for setting this pump can be displayed on the screen. This can include a simple "more" or "less", and/or may also include displaying a number field with a confirmation field. The operator can select the selection fields on the display in the manner already described and activate them by pressing the push-button. In this way, the operator can make entries on the medical device and thus operate it completely without touching it.

Embodiment with Two Radar Emitters

In addition to optical signals, other electromagnetic signals can also be used. Electromagnetic signals with small wavelengths such as radar, which can detect the smallest movement amplitudes, are advantageous. Radar sensor technology includes signal generators and receivers, each in the form of antennas or receiver coils.

In the following, one embodiment of the invention will be explained using the example of radar for electromagnetic waves. However, it will be apparent to those skilled in the art that other electromagnetic waves can also be used, or that the term radar can be broadly defined with respect to the wavelength range.

In the state of the art, radar sensor technology is regularly used for distance and motion detection, in which an emitted signal is evaluated in relation to a signal reflected by an object with regard to signal amplitude and phase relationship (temporal offset). A well-known application is the speed monitoring of vehicles. Recently, however, radar sensor technology has also been commercially offered that allows evaluations of the smallest movement amplitudes and can thus also be used to measure vital parameters of patients (see, for example, WO 18/167777 A1). The corresponding emitting and receiving units are sufficiently compact to be installed in a medical device in large numbers. One field of application of radar sensor technology is high-precision distance measurement.

To determine the distance to an object, for example, the principle of frequency modulated continuous wave radar (FMCW radar) can be used. This distance measurement includes the comparison of a reflected radar signal with a reference, usually a radiated radar signal. The distance can be determined via the propagation speed of radar waves (=$c_0$ speed of light) and the transit time between radiation and reception of the reflection. Due to the very high propagation speed and the relatively close distance in industrial applications, the direct determination of the propagation time is technically difficult. A way out is offered by the above-mentioned FMCW method, which uses a continuously frequency-varying signal as the excitation signal and instead of the propagation time uses the frequency difference between the exciting and reflected signal to measure the distance, which is technically more precise and less complex to implement.

Figure 1:
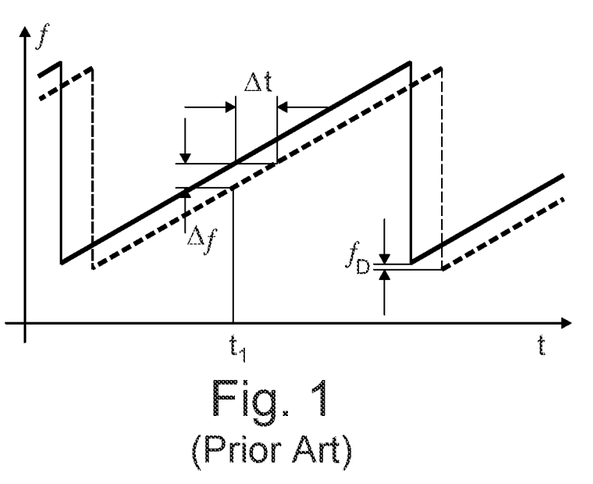
FIG. 1 depicts a relationship between emit and receive signals in the distance determination with a frequency modulated continuous wave (FMCW) radar.

In FMCW, the distance between the emitter/receiver and the measured object is determined according to the following relationship:

$$R = \frac{c_0 |\Delta t|}{2} = \frac{c_0 |\Delta f|}{2\left(\frac{d(f)}{d(t)}\right)}$$

wherein $c_0$=speed of light=$3\times10^8$ $^m$/s; $\Delta t$=propagation time [s]; $\Delta f$=measured frequency difference [Hz]; R=Distance antenna–object [m]; d(f)/d(t)=Frequency sweep per time unit.

Here, the frequency sweep per time unit is the slope of the frequency modulation, as shown in FIG. 1. The signal shown solid is an emission/reference signal and the signal shown dashed is a reflected signal.

Examples of radar-based distance measurement can be found in DE 102019002278A1, WO 2016/204641A1, WO 2020/127177A1, WO 9908128A1 and WO 07009833 A1.

Here, the FMCW measurement represents only an exemplary embodiment.

In order to make the above-described principle of contactless control also implementable with radar sensor technology, the medical device in one embodiment has at least three receivers (for determining the transmitter positions in space) sensitive to radar signals (or electromagnetic signals of specific wavelengths) and/or at least one emitter for an electromagnetic signal. Furthermore, the pointing pen has at least one emitter, as well as means for determining the position of the pointing axis with respect to the emitter. In one embodiment, this means is at least one further second emitter spatially remote from the first emitter. In a further embodiment, the pointing pen also comprises a receiver. In all embodiments, the pointing pen comprises a controller device and a power source. In further embodiments, the emitter also comprises input means for inputting information, analogous to the embodiments with laser emitters described further above.

Figure 2:
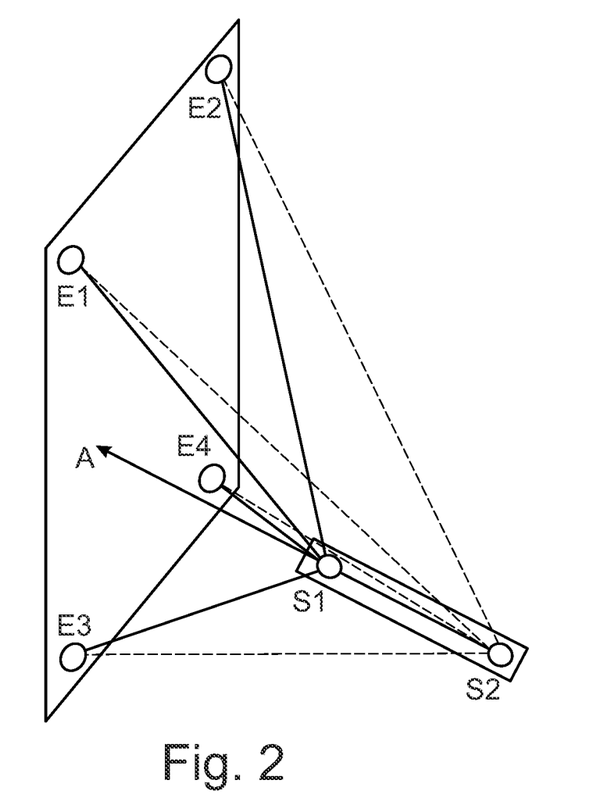
FIG. 2 depicts projection of the pointing pen axis onto the surface of the device according to embodiments of the invention.

Preferably, the embodiments of the invention based on the evaluation of electromagnetic beams are based on the determination of the position of the axis of the pointing pen with respect to the device that is to be operated and, derived therefrom, the determination of the position of the component of the medical device that is targeted by the operator, which can be determined by projecting the axis thus determined onto the surface of the device. This is illustrated in FIG. 2.

In this example, the medical device has four receivers (E1-E4). An emitter on the medical device is not shown here. The pointing pen has two emitter S1 and S2, which are arranged on the longitudinal axis of the stick. Via the method described below, the distance of the emitters S1 and S2 to each of the receivers can be determined (indicated by the solid and dashed lines from the receivers to the emitters) and thus the position of the pointing pen to the medical device can be determined by purely geometric calculations in the medical device. Thus, the projection of the longitudinal axis onto the surface of the device (arrow to A) can also be determined. The position in the example according to FIG. 2 results from the fact that the distances of the emitters S1 and S2 to the receivers E1-E4 can be determined and thus geometrically unambiguous pyramids result, the bases of which are formed by the rectangle at the corners of which the receivers E1-E4 are located and the respective tips of which are formed by the emitters S1 and S2. The position of the tips is defined by the distances to the individual receivers. The length of the pyramid edges corresponds exactly to the respective defined distance. Thus, for example, the coordinates of the emitters S1 and S2 can be determined in a reference space. With these coordinates, a vector can be determined on which the emitters S1 and S2 lie. By mathematically determining the intersection of this connection vector with the plane in the reference space on which the receivers E1-E4 lie, the point of impact A can be determined. Four receivers are shown in FIG. 2. At least three receivers are utilized to determine the point of impact.

Figure 3:
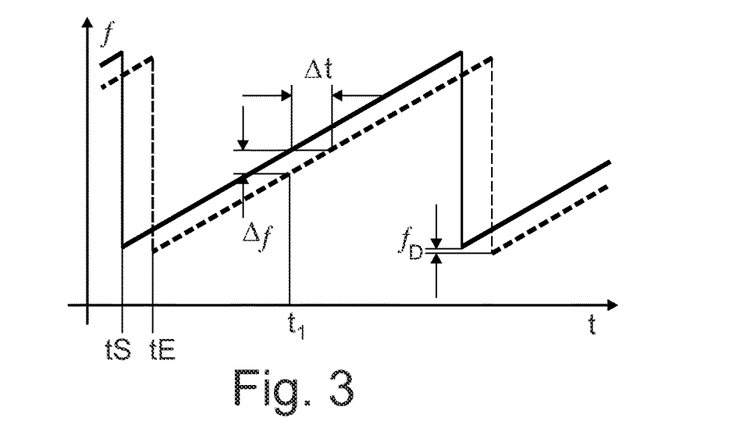
FIG. 3 depicts position determination of the pointing pen with the pointing pen signal triggered by a trigger signal according to embodiments of the invention.

In embodiments of the present invention, in order to obtain stable signals emitted by the pointing pen, no reflected radar signals are evaluated, but signals emitted directly by a pointing pen are evaluated in order to determine the position of the axis of the pointing pen by corresponding signal evaluation. To determine the distance to the point of emission, the signal emitted by the pointing pen behaves like a reflected signal. To achieve this, trigger signals are emitted from the medical device which, when received by the pointing pen, initiate the emission of the radar signals from the two emitters.

Referring to the FMCW embodiment and FIG. 3, this method comprises the following steps:

At time tS, the emitting apparatus emits an (arbitrary) electromagnetic trigger signal. The time tS is associated with the signal shown solid. The signal shown solid is only available as a reference signal path in the medical device and is not emitted. The signal shown in dashed lines is compared with this stored reference signal, e.g. the difference frequency is determined, from which the distance between emitter and receiver can be derived. The trigger signal can be emitted periodically to enable permanent position determination.

At the time (tS+tE)/2, the receiving apparatus of the pointing pen receives the trigger signal and immediately initiates the emission of the characteristic dashed signal, which is detected at the time tE at one of the receivers of the medical device. Via the comparison described above, the distance between the emitter and the respective receiver can be determined accordingly.

The triggering process may also be triggered by the pointing pen, for example by a movement detection in the pointing pen detecting a movement, emitting an activation signal via (any) emitter, which is received by the medical device, whereupon the medical device emits the trigger signal in the manner described above. In this way, no permanent triggering occurs, but only when movement of the pointing pen is detected.

It is not essential that emitter and receiver are arranged in the same place on the medical device. Consequently, a single emitter can be used on the medical device, which advantageously has the same distance to all receivers on the medical device. However, it is equally possible that combined emitting and receiving means (SE1-SE3, SE4) are used, which subsequently carry out the described method in order to determine the distance to the respective emitter of the pointing pen in each case.

If the pointing pen has two emitters S1 and S2, the distances to emitter 1 and emitter 2 can be determined one after the other, or simultaneously if non-overlapping frequency ranges are used. The duration of a measurement, i.e. approx. the modulation period T, is herein dimensioned so short that intermediate movements of the pointing pen are irrelevant. Although it is typical for FMCW measurement that the modulation period T is much larger than the propagation time of the signal, due to the speed of propagation (speed of light), the short distance (a few meters maximum) and the frequency range (several GHz; e.g. 85-100 GHz), the values are so small that the distance can be determined within the shortest time periods (e.g. <1 millisecond).

Figure 4:
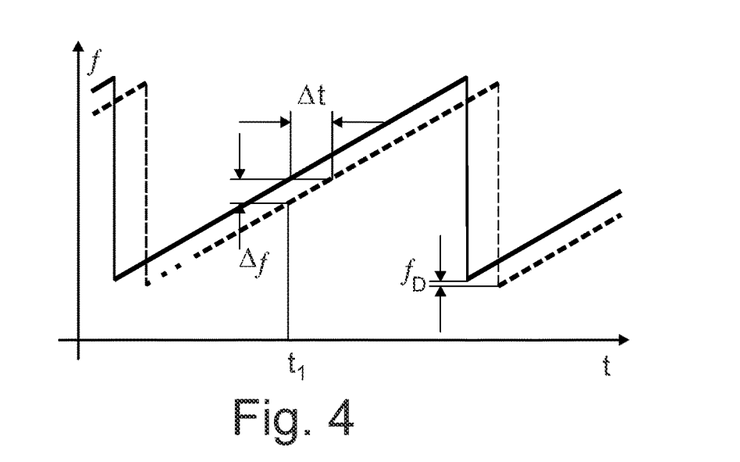
FIG. 4 depicts encoding of information in the pointing pen signal by characteristic interruption of the signal according to embodiments of the invention.

For transmission of additional information between the pointing pen and the medical device, the transmitted signal can also be used. This can be modulated as desired or modified or supplemented. For example, the signal of the pointing pen is characteristically interrupted and thus identifies the pointing pen. To determine the distance, it is not necessary for the emitted signal to completely contain all frequencies, as illustrated in FIG. 4.

Figure 5:
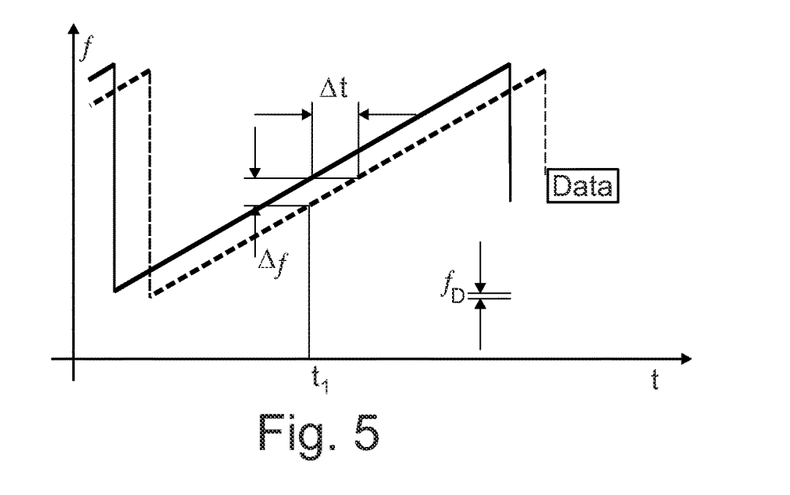
FIG. 5 depicts encoding of information in the pointing pen signal by appending the information to a modulation period in accordance with embodiments of the invention.

In this example, the dashed shown signal of the pointing pen comprises some gaps at the beginning, during which the signal is interrupted, but the determination of the time offset via the frequency difference of the two signal courses only takes place at a later point in time. The gaps in the return signal can encode information, e.g. about the user or the pointing pen. It is also possible to attach information to a modulation period, as shown in FIG. 5.

The data can be modulated onto the carrier signal in any way, for example as frequency or amplitudes or in a frequency-shift keying (FSK) method. The base frequency is also arbitrary. In the above example, this is within the spectrum of radar frequencies, which results in the same emitting apparatus can be used for distance determination and data transmission. The pointing pen may also have an additional emitter that is only set up for data transmission. The emission frequency of this emitter can be selected so that it does not overlap with the radiated radar waves. This means that the data transmission can also take place at the same time as the distance measurement.

As already described in the embodiment with laser emitter, in an analogous manner the pointing pen can be equipped with a push-button and authentication means. In this case, data transmission takes place as described above via the emitter/receiver means of the pointing pen and the medical device, which are sensitive to electromagnetic radiation and are not optical sensors.

Embodiment with a Radar Emitter and Angle Sensors

In another embodiment, the pointing pen comprises a single emitter and additional sensors for determining the inclination of the pointing pen in space and the angle that the axis of the pointing pen assumes with the earth's magnetic field. High-precision sensors are known to those skilled in the art for both variables, which are also available in sufficiently small versions to be integrated in a pointing pen according to the present invention. The integrated 360° angle sensor TLE5012B from Infineon and the inclination sensor STMicroelectronics IIS2ICLX are examples.

Figure 6:
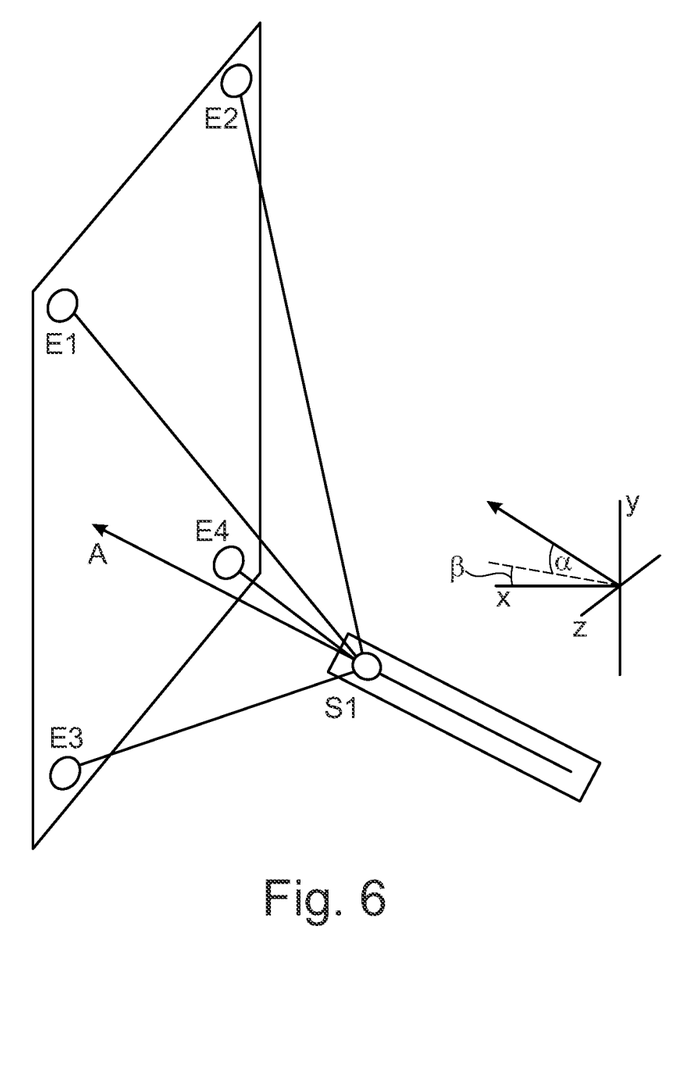
FIG. 6 depicts determining the inclination of the pointing pen with angular or inclination sensors according to embodiments of the invention.

If the position and orientation in relation to the spatial axes are also known to the medical device (which can be achieved with the aid of equivalent sensors), the point of impact of the projection of the pointing pen axis can also be clearly determined by emitting this information, as is shown in FIG. 6.

The angle and/or inclination sensors integrated in the pointing pen allow the angles $\alpha$ and $\beta$ to be unambiguously determined in relation to the reference axes x, y and z. If this information is transmitted to the medical device and the relative position of the device surface to the same reference axes is known, a control unit programmed accordingly for this purpose can calculate the point of impact taking into account the position of the emitter S1, which has also been determined, for example analogously to the method described above.

Since the relative position of the device surfaces to the above-mentioned reference axes can change due to translations or rotations of the device or individual device parts that are customary in practice, in particular due to an inclination of the screen, a dynamic calculation of the point of impact is at least advantageous. This can be achieved by modelling the device geometry, especially in relation to the receiver, and linking it to the calculation of the beam geometry. The modelled device geometry additionally allows the definition of active interaction points/surfaces corresponding to device elements that can be selected and influenced. Depending on the user and current device operating status, the active elements can be changed, enabling context-adaptive control.

Embodiment with Room/Area Monitoring

In the embodiments described above, the receiver apparatuses are arranged directly on the medical device. However, this is not absolutely necessary. The receiver apparatuses may be associated with the medical device, or the received signals may be associated with a medical device. For example, the receiver apparatuses may be mounted not as an integral part of a device to be operated, but within a room or area in which several devices may be located.

For example, receivers can be placed in the corners of the room to determine the position and pointing axis of the pointing pen in the above manner. If the room geometry, dimensions, position and orientation of the devices are known, it can be determined which device and which component is targeted, and control commands can be issued to them via a central control system. For this purpose, they are networked in terms of data technology. Here, too, the pointing pen can be assigned to specific persons and/or devices to be operated in order to enable or restrict operation.

This embodiment is particularly advantageous for large, stationary industrial plants where the position and orientation of the devices or components to be operated do not change.

This principle may not only be used for operation, but also for information acquisition. In this case, information about targeted system parts is transmitted to a device (tablet, smartphone) that is carried along. This can be, for example, operating data, maintenance data or general information. Such a method is particularly advantageous for large industrial plants where information about plant components is displayed centrally, but information is to be retrieved locally during operation.

The pointing apparatus may be integrated into the display apparatus carried along. For example, a smartphone could be used to point to a system component. With the aid of corresponding sensors, this can be detected in the above-mentioned manner, and information about the corresponding component can subsequently be sent to the smartphone via a networked central control system.

In certain exemplary embodiments, it is immaterial which method is used to determine the distance between the emitter and receiver. An amplitude evaluation of emitted electromagnetic waves of the emitters S1 and S2 and triangulation may also be used.

Directional emitting antennas for emitters S1 and S2 may be used, but this is not a prerequisite.

To avoid unwanted interference from several pointing sticks within a room, the frequency ranges of emitters S1 and S2 for each pointing pen can be selected so that they do not overlap with those of other pointing sticks. A receiving medical device recognizes the received frequency range and selects a corresponding reference signal accordingly. It can be provided that the received spectrum is divided into corresponding frequency ranges by signal filters in the medical device. In this way, for example, simultaneous operation of a device with several pointer sticks can be realized.

Another way to avoid unwanted interference is to time-multiplex the method for several pointing pens. This provides for assigning each pointing pen a periodic time range in which it can emit signals. This can be realized by a central time signal that is emitted and received by each pointing pen. The pointing pens can then be configured to be active only at certain time slots when no other pointing pen is active.

By the methods described, each device will notice whether or not a pointing pen is targeting one of its components, which may mean that it is targeting another device. Accordingly, it only becomes "active" in the first case. In this way, a single pointing pen can be used to control a wide variety of different devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The invention claimed is:

1. A system for contactless operation of a medical device, comprising:
    an electromagnetic pointing apparatus, comprising at least one electromagnetic signal emitter configured to emit a radar signal;
    at least three receivers configured to receive the radar signal emitted by the at least one electromagnetic signal emitter; and
    a processor configured to:
        determine a pointing target of the electromagnetic pointing apparatus relative to the medical device based on the received radar signal; and
        trigger a function of the medical device based on the determined pointing target of the electromagnetic pointing apparatus.

2. The system according to claim 1, wherein the processor is further configured to compare the radar signal with a reference signal.

3. The system according to claim 1, further comprising:
    an electromagnetic signal emitter associated with the medical device configured to emit a trigger signal to cause the electromagnetic pointing apparatus to emit the radar signal from the at least one electromagnetic signal emitter.

4. The system according to claim 1, wherein the processor is configured to perform a frequency modulated continuous wave (FMCW) method for determining a distance between the at least one electromagnetic signal emitter of the electromagnetic pointing apparatus and the at least three receivers.

5. The system according to claim 1, wherein the electromagnetic pointing apparatus further comprises at least a second signal emitter configured to emit a second radar signal and/or a sensor for determining an inclination of the electromagnetic pointing apparatus;
    wherein the electromagnetic pointing apparatus is further configured to determine a pointing axis of the electromagnetic pointing apparatus.

6. The system according to claim 1, wherein the electromagnetic pointing apparatus further comprises:
    at least one push-button; and
    a modulator configured to modulate information on the radar signal emitted by the at least one electromagnetic signal emitter in response to actuation of the at least one push-button.

7. The system according to claim 1, wherein the electromagnetic pointing apparatus further comprises a fingerprint scanner and/or a communication device configured to communicate with a fingerprint sensor wearable under a glove of an operator.

8. The system according to claim 1, wherein the at least three receivers are arranged at the medical device or arranged remotely relative to the medical device with a defined spatial relationship thereto.

* * * * *